US006303167B1

(12) United States Patent
Morris et al.

(10) Patent No.: US 6,303,167 B1
(45) Date of Patent: Oct. 16, 2001

(54) METHOD OF PRODUCING VITAMIN POWDERS

(75) Inventors: Charles A. Morris, Overland Park; Francis W. Calhoon, Jr., Olathe, both of KS (US); Huey L. Willis, Raymore, MO (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/188,166

(22) Filed: Nov. 9, 1998

(51) Int. Cl.$^7$ ...................................... A61K 9/14
(52) U.S. Cl. .................. 426/443; 424/442; 424/489; 426/96; 426/442; 514/458
(58) Field of Search .................. 424/442, 489; 423/335, 339; 426/96, 442, 443; 514/458, 904

(56) References Cited

U.S. PATENT DOCUMENTS

| | | |
|---|---|---|
| 1,638,700 | 8/1927 | Molofsky . |
| 2,162,609 | 6/1939 | Dawe .......................................... 99/4 |
| 2,257,545 | 9/1941 | Curtis ..................................... 252/129 |
| 2,385,075 | 9/1945 | Gunther ............................... 252/140 |
| 2,427,520 | 9/1947 | Briod et al. ................................. 99/6 |
| 2,650,202 | 8/1953 | Hawes et al. ........................ 252/449 |
| 2,708,163 | 5/1955 | Elton .......................................... 99/7 |
| 2,729,672 | 1/1956 | Callahan et al. ..................... 260/501 |
| 2,765,231 | 10/1956 | Plitt ........................................... 99/2 |
| 2,858,215 | 10/1958 | Espoy ........................................ 99/2 |
| 2,879,161 | 3/1959 | Valentine et al. ........................ 99/2 |
| 3,101,299 | 8/1963 | Ferrand .................................. 167/82 |
| 3,445,563 | 5/1969 | Clegg et al. ............................ 424/35 |
| 3,608,083 | 9/1971 | Bunnell et al. ...................... 424/284 |
| 3,646,192 | 2/1972 | Magid .................................... 424/35 |
| 3,914,430 | 10/1975 | Cannalonga et al. ................ 424/284 |
| 3,947,596 | 3/1976 | Cannalonga et al. ................ 424/344 |
| 3,959,472 | 5/1976 | Cannalonga et al. ................ 424/252 |
| 3,962,384 | 6/1976 | Cannalonga et al. .................... 264/7 |
| 4,010,073 | 3/1977 | Drake ..................................... 195/64 |
| 4,262,017 | 4/1981 | Kuipers et al. ...................... 424/284 |
| 4,395,422 | 7/1983 | Schmidt et al. ..................... 424/284 |
| 4,486,435 | 12/1984 | Schmidt et al. ..................... 424/252 |
| 4,519,961 | * 5/1985 | Schumacher et al. ................ 264/4.6 |
| 4,617,294 | 10/1986 | Krivak et al. .......................... 514/52 |
| 4,711,894 | 12/1987 | Wenzel et al. ....................... 514/458 |
| 5,179,122 | * 1/1993 | Greene et al. ...................... 514/458 |
| 5,234,695 | * 8/1993 | Hobbs et al. ........................ 424/489 |
| 5,318,903 | 6/1994 | Bewert et al. ....................... 435/187 |
| 5,635,214 | * 6/1997 | Ponchon et al. .................... 424/489 |
| 5,906,843 | * 5/1999 | Dew et al. ............................... 426/2 |
| 6,001,554 | * 12/1999 | Boyle et al. ............................ 435/4 |
| 6,146,825 | * 11/2000 | Boyle et al. ............................ 435/4 |
| 6,150,086 | * 11/2000 | Boyle et al. ............................ 435/4 |
| 6,162,474 | * 12/2000 | Chen et al. ............................ 426/72 |

FOREIGN PATENT DOCUMENTS 0 345 109 A1  12/1989  (EP) .

OTHER PUBLICATIONS

Shionogi and Co., Ltd., Japan, Japanese Patent No. JP 60–104012 A, entitled "Vitamins C and E combined formulations," *Chem. Abst.* 103:183564 (1985).
International Search Report for International Application No. PCT/US99/26397, mailed Mar. 24, 2000.

* cited by examiner

*Primary Examiner*—Robert H. Harrison
(74) *Attorney, Agent, or Firm*—Sterne, Kessler, Goldstein & Fox P.L.L.C.

(57) ABSTRACT

The present invention relates in general to a method of producing a dry, free-flowing mixture of liquid tocopherols. The present invention also relates to a dry free-flowing vitamin powder.

5 Claims, No Drawings

METHOD OF PRODUCING VITAMIN POWDERS

BACKGROUND OF THE INVENTION

1. Field of the Invention

The present invention relates in general to a method of producing dry, free-flowing mixtures of vitamin powders. The present invention also relates to a dry free-flowing vitamin powder.

2. Related Art

It is desirable to obtain free-flowing powders from fat-soluble or watersoluble vitamins. Such vitamin powders are commonly used as additives to feed mixtures or can be given to humans. Previous patents (U.S. Pat. Nos. 2,858,215, 4,617,294, 3,608,083, 3,914,430, 3,947,596, 3,959,472, 3,962,384, 4,395,422, 4,486,435) have provided methods for producing vitamin powders. A common drying technique used for producing vitamin powders is spray drying. The present invention provides a more economical method than spray drying to produce vitamin powders. Additionally, the invention provides a composition which has an extended shelf life and a higher level of mixed tocopherols than has been described in the prior art.

SUMMARY OF THE INVENTION

The invention provides a method of producing a dry, free-flowing vitamin powder comprising blending redried corn starch, silica and at least one vitamin in a blender, wherein said corn starch and silica are blended and said vitamin are added to make a composition.

The invention also provides a method of producing a dry, free-flowing vitamin powder comprising blending silica and at least one vitamin in a blender wherein said silica has a density of at least 12.5 lbs/cu. ft., a particle size of between 40 and 50 microns and a BET surface area of from about 400 $m^2/g$ to 500 $m^2/g$.

The invention further provides a method of producing a dry, free-flowing vitamin powder comprising mixing silica and at least one vitamin in a blender which has at least 3600 rotations per minute (rpm).

The invention also provides a method of producing a dry, free-flowing vitamin powder comprising mixing silica and liquid mixed tocopherols wherein said tocopherols are present in amounts greater than 50 to about 80 weight percent.

The invention further provides a composition comprising about 5 to about 34 weight percent redried corn starch, silica and at least one vitamin.

The invention also provides a composition comprising silica wherein said silica has a density of at least 16.8 lbs/cu. ft., a particle size minimum of 125 microns and at least one vitamin.

The invention also provides a composition comprising silica and at least one vitamin in amounts from about 50 to about 80 weight percent.

DETAILED DESCRIPTION OF THE PREFERRED EMBODIMENTS

In one embodiment, the present invention relates to a method of producing a dry free-flowing powder from liquid vitamins by blending redried corn starch, wheat starch, silica and at least one vitamin in a blender. Preferably, the above-described method comprises (a) mixing redried corn starch and silica in a blender and (b) adding at least one vitamin to said redried corn starch and silica mixture. In the present invention "blend" is intended to be synonymous with "mix": to join or combine two or more components into a single mass. One advantage of the above and below-described methods is a 10 percent cost reduction in manufacturing over spray dried vitamin powders. Similarly, equipment costs for the present invention would be lower than the cost of a spray drier.

The invention further provides compositions comprising corn starch, silica and at least one vitamin. The compositions of the present invention have extended shelf lives of over nine months and higher levels of mixed tocopherols than has been described in the prior art. The product wets out better, has improved dispersion in solution, improved uniformity and the particle size is more compatible with other nutritional products.

The invention further relates to the above and below-described methods and compositions wherein said vitamin may be preheated prior to blending with corn starch and silica, preferably to at least 130° C.

The vitamin-containing powders of the present invention may contain as their active vitamin ingredient any suitable vitamin, including an oil-soluble vitamin or mixture thereof, a water-soluble vitamin or mixture thereof, or mixtures of water and fat soluble vitamins. "Vitamin" may be defined as a trace organic substance required in the diet of some species for proper growth and function. In the present invention, the above and below-described methods and compositions provide use of fat and/or water soluble vitamins comprising at least one vitamin selected from the group consisting of: vitamin A, vitamin D, vitamin E, vitamin K, vitamin C, vitamin $B_1$, vitamin $B_2$, vitamin $B_6$, vitamin $B_{12}$, folic acid, biotin, inositol, beta carotene, vitamin $B_3$, and vitamin $B_5$, and mixtures thereof. Preferably said vitamin comprises a mixed tocopherol composition, and more preferably, a mixed tocopherol composition with a minimum assay of 100 mg/g mixed tocopherols, and even more preferably, with a minimum assay of 400 mg/g mixed tocopherols, and most preferably, with a minimum assay of 700 mg/g tocopherols Vitamin E is composed of at least three molecular species. The amounts of d-alphas, d-beta, d-gamma, and d-delta tocopherol can vary because of natural variation of the oil. But the typical value would be d-alpha 14%, d-beta 1%, d-beta 1%, d-gamma 62% and d-delta 23%. "Mixed tocopherols" is a composition of these molecular species. Mixed tocopherols may be obtained commercially (Henkel Corp. and ADM Co.).

The vitamins and vitamin mixtures of the above and below-described methods and compositions may be present in amounts from about 0.02 to about 90 weight percent, preferably about 20 to about 90 weight percent, more preferably about 40 to about 90 weight percent, more preferably greater than about 50 to about 80 weight percent, and most preferably from about 60 to about 80 weight percent.

As the binder or filler in the vitamin powders, generally any starch which is at least partially soluble in water at ambient temperature can be employed in the vitamin powders made by the above and below-described methods. Corn starch is one type of binder that may be used; it is a fine, granular or powdery starch which enhances the flow properties of the vitamin powders of the invention. Prior to use, the corn starch should have a moisture of 7.5%. The invention provides the above and below-described methods and compositions wherein said corn starch is present in amounts from about 5 to about 90 weight percent, preferably, in amounts from about 5 to about 34 weight percent.

Certain vitamins are absorbed onto inert carriers such as silica, and the resulting absorbate product is mixed or blended with United States Pharmaceutical (USP), Food Chemical Codex (FCC), or grass products (FDA safe supplement). The carrier must be chemically inert with respect to the vitamin with which it is mixed and also harmless to the animal who ingests the absorbate product. Vitamin E mixtures are also suitable for use as anti-oxidants to protect various materials such as lard and vegetable oils. Silica is particularly suitable as carrier for vitamins because it is essentially inert with respect to many vitamins and harmless to the animal or human who ingests the adsorbate product. Silica (empirical formula $SiO_2$, silicon dioxide) is a white, granular, bead-like powder that is dry to the touch. Despite appearing dry, the silica normally contains two different types of bound water which may be removed by heating. "Free water" may be removed by heating to at least 105° C. for approximately 24 hours, whereas "bound water" may be removed by heating to between 1000° C. and 1200° C. for approximately 24 hours. Chemically, the silica contains at least 99 weight percent of $SiO_2$. The invention provides the above and below-described methods and compositions wherein said silica has a density of at least 200 g/l, a particle size of between 40 and 50 microns, and a surface area of from about 400 $m^2/g$ to 500 $m^2/g$.

The invention also provides a method of producing a dry, free-flowing vitamin powder comprising mixing silica and at least one vitamin in a blender wherein said silica has a density of at least 16.8 lbs/cu. ft., a particle size of a minimum of 125 microns.

In a further embodiment, the present invention provides a method of producing a dry, free-flowing vitamin powder comprising mixing silica and liquid mixed tocopherols wherein said tocopherols are present in amounts greater than 50 to about 80 weight percent.

In another embodiment, the present invention relates to a method of producing a dry, free-flowing vitamin powder comprising mixing silica and at least one vitamin in a blender which has an rpm of at least 3600 etc. The plow inside the mixer is used to blend the silica and starch. Then as the liquid tocopherol is added, the chopper is run at a minimum of 3600 rpm for dispersion. In the present invention "blender(s)" are intended to include both blenders and mixers and/or any equipment means useful for the mixing or blending of any liquid/solid, solid/solid or liquid/liquid materials. Such blenders include Warring blenders and Littleford mixers, Turbulizer and Walters. The invention also provides a composition comprising silica and at least one vitamin.

The present invention is described in fer detail in the following non-limiting examples.

EXAMPLE 1

Liquid 70 percent mixed tocopherols, minimum assay of 700 mg/g (Covi-Ox T70, Henkel Corp.) in an amount of 57 weight percent was added to silica (Sipemat 225, Degussa) in a beaker. After hand mixing, the contents of the beaker were transferred to a Warring Blender and mixed at high speed until uniform.

EXAMPLE 2

Liquid 70 percent mixed tocopherols, minimum assay of 700 mglg (Covi-Ox T70, Henkel Corp.) in an amount of 72 weight percent was added to silica (Sipemat 225, Degussa) in a beaker. After hand mixing, the contents of the beaker were transferred to a Warring Blender and mixed at high speed until uniform.

EXAMPLE 3

Silica (Sipernat 50, Degussa) in an amount of 22.5 weight percent and redried corn starch in an amount of 33.64 weight percent were blended in a mixer (Model FM-130-D, Littleford). Seventy percent mixed tocopherols (MTS-70, Archer-Daniels-Midland Co.) in an amount of 43.86 percent were heated to 130° F. The heated tocopherols were blended with the silica and redried corn starch by slowly mixing only with the plows of the mixer. After all of the liquid tocopherols were added to the mixer, the mixer was ran at high speed for 3 minutes using the plows and chopper.

EXAMPLE 4

Silica (Sipernat 50, Degussa) at 30 weight percent and redried corn starch in an amount of 5 weight percent were blended in a mixer (Model FM-130-D, Littleford). Seventy percent mixed tocopherols (MTS-70, Archer-Daniels-Midland Co.) in an amount of 65 percent were heated to 130° F. The heated tocopherols were blended with the silica and redried corn starch by slowly mixing only with the plows of the mixer. After all of the liquid tocopherols were added to the mixer, the mixer was run at high speed for 3 minutes using the plows and chopper.

EXAMPLE 5

Silica (Sipernat 50, Degussa) at 30 weight percent and redried corn starch in an amount of 5 weight percent were blended in a mixer (Model FM-130-D, Littleford). Seventy percent mixed tocopherols (MTS-70, Archer-Daniels-Midland Co.) in an amount of 65 percent were heated to 130° F. The heated tocopherols were blended with the silica and redried corn starch by slowly mixing only with the plows of the mixer. After all of the liquid tocopherols were added to the mixer, the mixer was run at high speed for 3 minutes using the plows and chopper.

EXAMPLE 6

The products produced from Examples 1–5 were dry and free-flowing. The sample was stored at room temperature without special protection from light or air. A 30 percent dry mixed tocopherols sample (Example 3) was assayed for percent mixed tocopherols 4 times over approximately 11 months. This sample showed a small loss of mixed tocopherols over 11 months (from 29.72% to 28.84%).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of producing a dry, free-flowing vitamin powder comprising mixing silica and liquid mixed tocopherols, wherein said liquid mixed tocopherols are present in amounts of 65 to about 80 weight percent of said vitamin powder, and wherein said silica has a particle size of between 40 and 50 microns.

2. The method of claim 1, wherein said liquid mixed tocopherols are heated prior to mixing.

3. The method of claim 1, wherein said mixing silica and liquid mixed tocopherols occurs in a blender, wherein said blender is mixing at an rpm of at least 3600.

4. The method of claim 1, comprising mixing redried cornstarch and said silica and said liquid mixed tocopherols.

5. The method of claim 4, wherein said redried corn starch is present in amounts from about 5 to about 34 weight percent of said vitamin powder.

* * * * *